United States Patent
Eck et al.

(10) Patent No.: US 6,596,901 B1
(45) Date of Patent: *Jul. 22, 2003

(54) METHOD FOR PURIFYING ACRYLIC ACID AND METHACRYLIC ACID

(75) Inventors: Bernd Eck, Viernheim (DE); Otto Machhammer, Mannheim (DE); Theo Proll, Bad Dürkheim (DE); Volker Schliephake, Schifferstadt (DE); Klaus Joachim Müller-Engel, Stutensee (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/147,484
(22) PCT Filed: Jul. 9, 1997
(86) PCT No.: PCT/EP97/03630
§ 371 (c)(1), (2), (4) Date: Jan. 5, 1999
(87) PCT Pub. No.: WO98/01415
PCT Pub. Date: Jan. 15, 1998

(30) Foreign Application Priority Data

Jul. 10, 1996 (DE) .......................................... 196 27 847

(51) Int. Cl.[7] .............................................. C07C 51/42
(52) U.S. Cl. ....................................................... 562/600
(58) Field of Search ......................................... 562/600

(56) References Cited

U.S. PATENT DOCUMENTS

| 4,156,633 | A | * | 5/1979 | Horlenko et al. ............ 562/600 |
| 4,599,144 | A | * | 7/1986 | Baleiko et al. .............. 562/600 |
| 4,780,568 | A | * | 10/1988 | Pascoe ........................ 562/600 |
| 5,426,221 | A | * | 6/1995 | Willersinn ................... 562/600 |
| 5,504,247 | A | * | 4/1996 | Saxer et al. ................. 562/600 |
| 5,831,124 | A | * | 11/1998 | Machhammer et al. ..... 562/600 |
| 6,448,439 | B1 | * | 9/2002 | Eck et al. |

* cited by examiner

Primary Examiner—Alan L. Rotman
Assistant Examiner—Taylor V Oh
(74) Attorney, Agent, or Firm—Oblon, Spivak, McClelland, Maier & Neustadt, P.C.

(57) ABSTRACT

A process for preparing acrylic acid or methacrylic acid comprises
(a) preparing a gaseous product mixture having essentially the composition of a reaction mixture of the catalytic gas phase oxidation of $C_3$-/$C_4$-alkanes, -alkenes, -alkanols and/or -alkanals and/or precursors thereof to form acrylic acid or methacrylic acid, characterized by
(b) condensing said product mixture,
(c) crystallizing acrylic acid or methacrylic acid from the solution obtained in step (b), and
(d) removing the resulting crystals from the mother liquor.

21 Claims, 1 Drawing Sheet

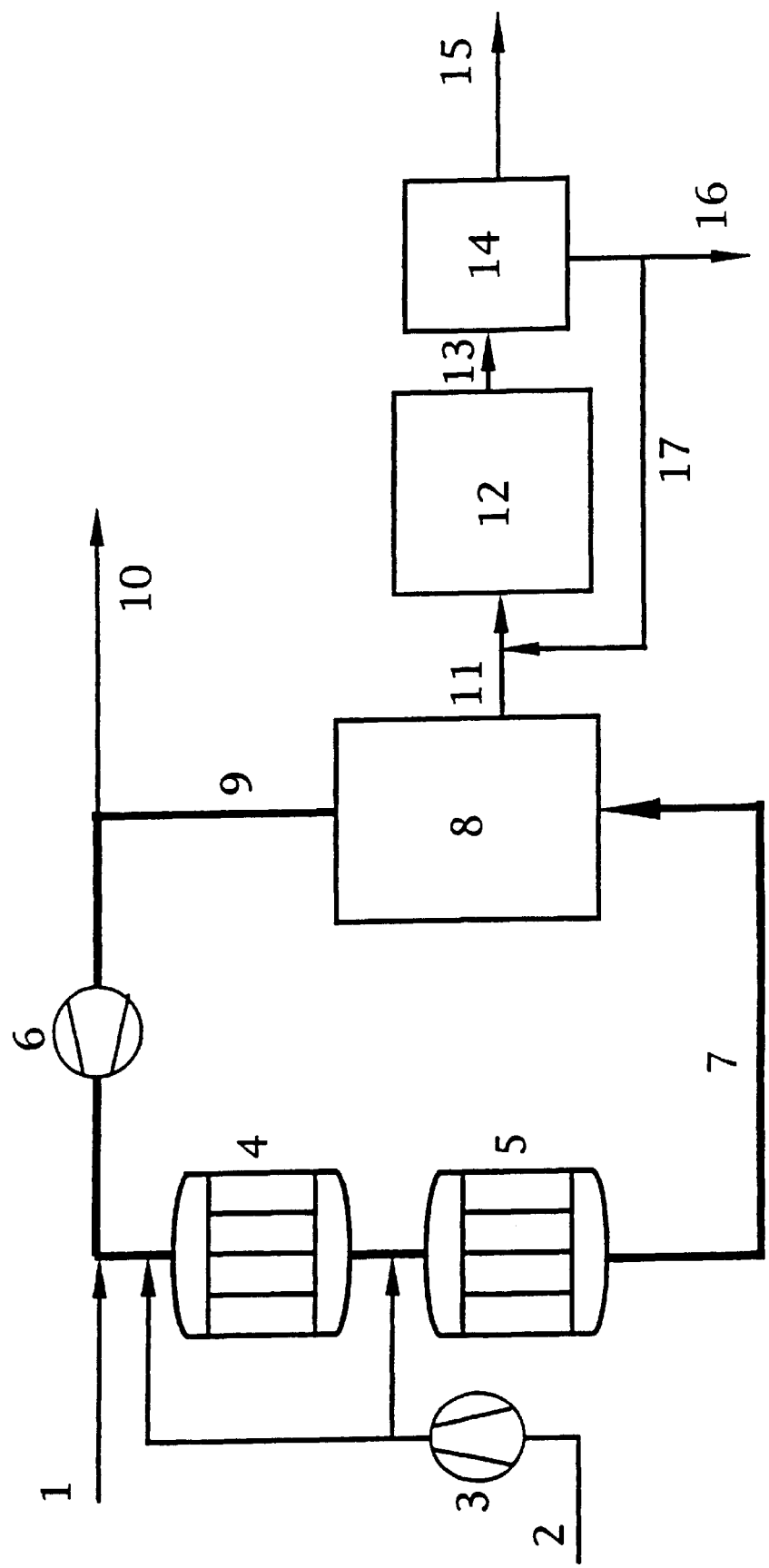

METHOD FOR PURIFYING ACRYLIC ACID AND METHACRYLIC ACID

The present invention relates to a process for preparing acrylic acid and methacrylic acid.

Acrylic acid is a major basic chemical product. Owing to its very reactive double bond and the acid function, it is particularly useful as a monomer for preparing polymers. The bulk of acrylic acid monomer production is esterified prior to polymerization, for example to make adhesives, dispersions or coatings. Just a fraction of acrylic acid monomer production is polymerized directly, for example to make superabsorbents. Whereas, in general, the direct polymerization of acrylic acid requires high purity monomer, acrylic acid purity requirements are not so high if the acrylic acid is esterified before it is polymerized.

It is common knowledge that acrylic acid can be produced by heterogeneously catalyzed gas phase, oxidation of propene with molecular oxygen over solid catalysts at from 200 to 400° C. in two stages via acrolein (cf eg. DE-A-1 962 431, DE-A-2 943 707, DE-C-1 205 502, DE-A-195 08 558, EP-A-0 257 565, EP-A-0 253 409, DE-A-2 251 364, EP-A-0 117 146, GB-B-1 450 986 and EP-A-0 293 224). The catalysts used are oxidic multicomponent catalysts based, for example, on oxides of the elements molybdenum, bismuth and iron (in stage 1) or molybdenum and vanadium (in stage 2).

DE-C-2 136 396 discloses removing the acrylic acid from the reaction gases obtained by catalytic gas phase oxidation of propene or acrolein by countercurrent absorption with a mixture of 75% by weight of diphenyl ether and 25% by weight of biphenyl. DE-A-2 449 780 describes cooling the hot reaction gas by partial evaporation of the solvent in a direct condenser (quench apparatus) prior to the countercurrent absorption. The problem here is, as with further process steps, the production of solids in the apparatus, reducing plant availability. According to DE-A-4 308 087, this production of solids can be reduced by adding a polar solvent such as dimethyl phthalate in an amount of from 0.1 to 25% by weight to the relatively a polar solvent mixture of diphenyl ether and biphenyl.

In addition to the above-described absorption of the reaction product comprising acrylic acid into a high boiling solvent mixture, other known processes envisage a total condensation of acrylic acid and of the water of reaction formed in the course of the catalytic oxidation. This gives rise to an aqueous acrylic acid solution which can be further worked up via distillation with an azeotrope (cf DE-C-3 429 391, JP-A-1 124 766, JP-A-7 118 766, JP-A-7 118 966-R, JP-A-7 118 968-R and JP-A-7 241 885) or via an extraction process (cf DE-A-2 164 767, JP-A-5 81 40-039, JP-A-4 80 91 013). In EP-A-0 551 111, the mixture of acrylic acid and by-products produced by means of catalytic gas phase oxidation is contacted with water in an absorption tower and the resulting aqueous solution is distilled in the presence of a solvent that forms an azeotrope with polar low boilers such as water or acetic acid. DE-C-2 323 328 describes removing acrylic acid from an acidified, aqueous butanol/acrylic acid esterification waste liquor by extraction with a specific mixture of organic solvents.

The processes described above have the disadvantage of employing for the extraction or absorption an organic solvent which has to be removed again in a further operation, such as a rectification, under high thermal stress. This may cause the acrylic acid to polymerize.

JP-A-7 082 210 describes a process for purifying an acrylic acid comprising acetic acid, propionic acid, acrolein and furfural as well as acrylic acid. This process comprises adding water and then crystallizing under reduced pressure to obtain a purity of 99.6% for the acrylic acid crystals after removal and washing. Japanese Patent 45-32417 discloses a process wherein an aqueous acrylic or methacrylic acid solution additionally comprising acetic acid and propionic acid is extracted with heptane or toluene before water is removed from the extract by distillation. In the next step, the remaining extract is cooled down to −20 to −80° C. to bring about a crystallization of acrylic acid or methacrylic acid. The crystals are removed, and the mother liquor is recycled into the extraction process. According to this patent, it is necessary to use an organic solvent or extractant, since the solution otherwise solidifies on cooling without forming crystals. This process is disadvantageous in that, as well as requiring the addition of an organic solvent, a distillation has to be carried out to remove water. Canadian Patent 790 625 relates to a further purification process for crude acrylic acid by fractional crystallization. In this process, if propionic acid is the main impurity in the crude acrylic acid, the temperature is not reduced below the peritectic temperature of the acrylic acid/propionic acid system, whereas it is not reduced below the eutectic temperature of the acrylic acid/acetic acid system when acetic acid is the main impurity. The acrylic acid used for crystallization in this process is prepared by conventional processes, for example by gas phase oxidation of propene or acrolein, and then subjected to a prepurification by conventional known processes, for example extraction. The crystallization of acrylic acid is said to be preferably carried out in the substantial absence of water.

EP-A-0 616 998 describes a process for purifying acrylic acid by a combination of dynamic and static crystallization of a prepurified acrylic acid, for example an acrylic acid which has been prepurified by distillation.

Common to the processes described in the above documents is that they require a (pre)purification of the acrylic acid prior to crystallization. Since the prepurification generally utilizes organic solvents which have to be subsequently separated off again under high thermal stress, there is always the risk of the acrylic acid undergoing premature polymerization.

EP-A-0 002 612, which relates to a process for purifying acrylic acid in aqueous solution by fractional crystallization, discloses the addition of salts to the acrylic acid solution so as to break up the water/acrylic acid eutectic system which exists at an acrylic acid content of 63% by volume.

EP-A-0 675 100 describes a process for preparing $\alpha,\beta$-unsaturated $C_3$–$C_6$-carboxylic acids, eg. methacrylic acid, by oxidative dehydrogenation of the corresponding saturated $C_3$–$C_6$-carboxylic acid, followed by melt crystallization with subsequent fractional distillation or followed by fractional distillation with subsequent melt crystallization.

It is an object of the present invention to provide a process for obtaining acrylic acid or methacrylic acid in high purity without complex operations.

We have found that this object is achieved, surprisingly, by a process whereby acrylic acid or methacrylic acid from a gaseous product mixture which has been subjected to a condensation can be crystallized directly from the solution formed in the condensation. More particularly, the process found requires no further purifying step and no addition of assistants.

The present invention accordingly provides a process for preparing acrylic acid or meth-acrylic acid, which comprises (a) preparing a gaseous product mixture having essentially the composition of a reaction mixture of the catalytic gas phase oxidation of $C_3$-/$C_4$-alkanes, -alkenes, -alkanols and/or -alkanals and/or precursors thereof to form acrylic acid or methacrylic acid, (b) condensing said gaseous product mixture, (c) crystallizing acrylic acid or methacrylic acid from the solution obtained in step (b), and (d) removing the resulting crystals from the mother liquor.

In a preferred embodiment, at least a portion of the mother liquor is recycled into step (c) (step (e)). Further preferred embodiments of the invention will be apparent from the description which follows, the subclaims, the drawing and the Example.

In the process of the present invention, acrylic acid or methacrylic acid is crystallized directly and unmediatedly without further intermediary or purifying steps and without addition of assistants from the solution which is formed in the course of the condensation of the product mixture. This product mixture has essentially the composition of a reaction product formed in a catalytic gas phase oxidation process to form the acid.

The sole figure illustrates a preferred embodiment of carrying out the process of the present invention.

Step (a)

Step (a) produces a gaseous product mixture which essentially has the composition of a reaction mixture of the catalytic gas phase oxidation of $C_3$- or $C_4$-alkanes, -alkenes, -alkanols and/or -alkanals and/or precursors thereof to form acrylic acid or methacrylic acid. It is particularly advantageous for the gaseous product mixture to be prepared by catalytic gas phase oxidation of propene, acrolein, tert-butanol, isobutene, isobutane, isobutyraldehyde, methacrolein, isobutyric acid or methyl tert-butyl ether. Suitable starting compounds include all precursors of the aforementioned compounds from which the actual $C_3/C_4$ starting compound is formed as an intermediate during the gas phase oxidation. Examples which may be mentioned here are methyl tert-butyl ether and isobutyric acid for the production of methacrylic acid.

A particularly advantageous source of the gaseous product mixture to be used in the process of the present invention is the catalytic gas phase conversion of propene and/or acrolein into acrylic acid using molecular oxygen according to known processes, especially as described in the above-cited references. This gas phase reaction is preferably carried out at from 200 to 450° C. with or without superatmospheric pressure. The heterogeneous catalysts used are preferably oxidic multicomponent catalysts based on the oxides of molybdenum, bismuth and iron in stage 1 (oxidation of propene to acrolein) and the oxides of molybdenum and vanadium in stage 2 (oxidation of acrolein to acrylic acid). When propane is used as a starting material, it can be converted into a propene/propane mixture by: catalytic oxydehydrogenation as described, for example, in Catalysis Today 24 (1995), 307–313, or U.S. Pat. No. 5,510,558; by homogeneous oxydehydrogenation, as described for example, in CN-A-1 105 352; or by catalytic dehydrogenation as described, for example, in EP-A-0 253 409, EP-A-0 293 224, DE-A-195 08 558 or EP-A-0 117 146. When a propene/propane mixture is used, propane acts as diluent. Further suitable propene/propane mixtures are refinery propene (70% of propene and 30% of propane) or cracker propene (95% of propene and 5% of propane). In principle, propene/propane mixtures such as those mentioned above can be oxidized with oxygen or air or a mixture of oxygen and nitrogen of any composition to acrolein and acrylic acid.

The conversion of propene into acrylic acid is strongly exothermic. The reaction gas, which as well as the starting materials and the products advantageously includes an inert diluent gas, for example recycle gas (see below), atmospheric nitrogen, one or more saturated $C_1$–$C_6$-hydrocarbons, especially methane and/or propane, and/or water vapor, can therefore absorb only a small fraction of the heat of reaction. Although the type of reactor used is not subject to any restriction per se, it is common to use tube bundle heat exchangers packed with the oxidation catalyst, since with this type of apparatus the predominant fraction of the heat of reaction can be removed to the cooled tube walls by convection and radiation.

The catalytic gas phase oxidation process produces not pure acrylic acid, but a gaseous mixture which, as well as acrylic acid, may essentially include as secondary components unconverted acrolein and/or propene, water vapor, carbon monoxide, carbon dioxide, aitrogen, propane, oxygen, acetic acid, propionic acid, formaldehyde, further aldehydes and maleic anhydride. The reaction product mixture customarily comprises (each percentage based on the total reaction mixture) from 1 to 30% by weight of acrylic acid, from 0.05 to 1% by weight of propene and from 0.05 to 1% by weight of acrolein, from 0.05 to 10% by weight of oxygen, from 0.05 to 2% by weight of acetic acid, from 0.01 to 2% by weight of propionic acid, from 0.05 to 1% by weight of formaldehyde, from 0.05 to 2% by weight of aldehydes, from 0.01 to 0.5% by weight of maleic anhydride and from 20 to 98% by weight, preferably from 50 to 98% by weight, of inert diluent gases. The inert diluent gases present include, in particular, saturated $C_1$–$C_6$-hydrocarbons, such as from 0 to 90% by weight of methane and/or propane, and also from 1 to 30% by weight of water vapor, from 0.05 to 15% by weight of carbon oxides and from 0 to 90% by weight of nitrogen, each percentage being based on 100% by weight of diluent gas.

Methacrylic acid can be prepared similarly to acrylic acid by catalytic gas phase reaction of $C_4$ starting compounds with molecular oxygen. A particularly advantageous way to obtain methacrylic acid is, for example, by catalytic gas phase oxidation of isobutene, isobutane, tert-butanol, isobutyraldehyde, methacrolein or methyl tert-butyl ether. The catalysts used are again transition metal mixed oxide catalysts (eg. Mo, V, W and/or Fe). Particularly suitable processes for producing methacrylic acid are those which are based on methacrolein, especially when the methacrolein is produced by gas phase catalytic oxidation of tert-butanol, isobutane or isobutene or by reaction of formaldehyde with propionaldehyde as described in EP-B-0 092 097 or EP-B-0 058 927. It is thus possible to prepare methacrylic acid in two stages by (1) condensation of propionaldehyde with formaldehyde (in the presence of a secondary amine as catalyst) to form methacrylic acid and (2) subsequent oxidation of the meth-acrolein to methacrylic acid.

As with the production of acrylic acid, the product is not pure methacrolein, but a gaseous mixture which, as well as methacrylic acid, may essentially include as secondary components unconverted methacrolein and/or water vapor, carbon monoxide, carbon dioxide, nitrogen, oxygen, acetic acid, propionic acid, further aldehydes and maleic anhydride. The process of the present invention is used especially when the reaction mixture comprises from 0.02 to 2% by weight of methacrylic acid, based on the total reaction mixture, and otherwise essentially the same corresponding constituents as with the production of acrylic acid.

Step (b)

Step (b) subjects the reaction product of step (a) to a condensation, particularly to a partial or total condensation, to obtain a solution. The condensation can be effected in one or more stages according to customary processes, and the type of condensation is not subject to any special restriction. The condensation is advantageously carried out in a direct condenser where previously produced condensate is contacted with the hot gaseous reaction product. Suitable apparatuses for the condensation are in particular spray scrubbers, Venturi scrubbers, bubble columns or apparatuses having betrickled surfaces.

The mixture obtained by partial or total condensation of the reaction product of step (a) preferably comprises from 60 to 99.5% by weight of acrylic or methacrylic acid, from 0.1 to 40% by weight of water, and also from 0.1 to 15% by weight of impurities, especially, each percentage being based on 100% by weight of condensate, from 0.01 to 5% weight of acrolein or methacrolein, from 0.05 to 5% by weight of acetic acid, from 0.01 to 5% by weight of propionic acid, from 0.01 to 5% by weight of formaldehyde, from 0.01 to 5% by weight of further aldehydes and from 0.01 to 5% by weight of maleic acid. It is particularly preferable for the condensation to afford a mixture comprising from 93 to 98% by weight of acrylic or methacrylic acid, from 1 to 5% by weight of water, and also from 0.5 to 5% by weight of impurities, especially, each percentage being based on 100% by weight of condensate, from 0.01 to 3% by weight of acrolein or methacrolein, from 0.1 to 3% by weight of acetic acid, from 0.01 to 3% by weight of propionic acid, from 0.01 to 3% by weight of formaldehyde, from 0.01 to 3% by weight of further aldehydes and from 0.01 to 3% by weight of maleic acid.

Step (c)

Step (c) crystallizes the solution obtained in step (b), which comprises acrylic acid or methacrylic acid. Thus, the solution obtained in the condensation step is fed directly to the crystallization step. No solvent is added, especially no organic solvent. The crystallization process used is not subject to any restriction. The crystallization can be carried out continuously or batchwise, in one or more stages. The crystallization is preferably carried out in a single stage. In another preferred embodiment of the invention, the crystallization is carried out as a fractional crystallization. In the art of fractional crystallization it is customary to term all stages which produce a crystallizate which is purer than acrylic or methacrylic acid solution feed purifying stages and all other stages stripping stages. Multi-stage fractional crystallization processes are advantageously operated according to the countercurrent principle whereby the crystallizate is separated from the mother liquor in each stage and fed to the particular stage having the next higher degree of purity, while the crystallization residue is fed to the particular stage having the next lower degree of purity.

The temperature of the solution during the crystallization is advantageously within the range from −25° C. to +14° C., especially within the range from 12° C. to −5° C. The solids content in the crystallizer is advantageously within the range from 0 to 80 g of solids/100 g, preferably within the range from 15 to 35 g of solids/100 g.

In an advantageous embodiment of the invention, the crystallizing is effected by cooling apparatus walls or by evaporating the solution under reduced pressure. In the case of the crystallizing by cooling, the heat is removed via scrape coolers connected to a stirred tank or to a vessel without stirrer. The circulation of the crystal suspension is ensured in this case by means of a pump. Alternatively, it is possible to remove the heat via the walls of a stirred tank having a close-clearance stirrer. A further preferred embodiment of cooling crystallization involves the use of cooling disc crystallizers as manufactured for example by Gouda (Netherlands). In a further suitable variant for crystallization by cooling, the heat is removed via conventional heat transferors (preferably tube bundle or plate heat transferors). These apparatuses, unlike scraped-surface coolers, stirred tanks having close-clearance stirrers or cooling disc crystallizers, have no means for avoiding crystal layers on the heat-transferring surfaces. If, in operation, a state is reached where the heat transfer resistance has become too high due to crystal layer formation, the operation is switched over to a second apparatus. During operation of the second apparatus, the first apparatus is regenerated (preferably by melting off the crystal layer or by flushing the apparatus through with unsaturated solution). If heat transfer resistance becomes too high in the second apparatus, operation is switched back again to the first apparatus, etc. This variant can also be operated with more than two apparatuses in alternation. In addition, the crystallization can be effected by conventional evaporation of the solution under reduced pressure. In a further advantageous embodiment of the invention, a crystallization takes place in apparatuses in which the crystals grow on cooled surfaces within the crystallization apparatus, ie. are immobilized in the apparatus (eg. layer crystallization process of Sulzer Chemtech (Switzerland) or static crystallization process of BEFS PROKEM (France)).

Step (d)

Step (d) separates the acrylic or methacrylic acid crystals obtained in step (c) from the mother liquor. For a layer crystallization or a static crystallization, the separation of the crystals from the mother liquor can take place in the crystallization apparatus itself, since the crystals are immobilized in the apparatus and the mother liquor can be removed from the apparatus by letting it flow out. The crystals are removed from the crystallization apparatus by melting the crystals and then letting the melt flow out. For a suspension crystallization, any known solid-liquid separation is suitable. In a preferred embodiment of the invention, the crystals are separated from the mother liquor by filtration and/or centrifugation. Advantageously, the filtration or centrifugation is preceded by a (pre)thickening of the suspension, for example by means of one or more hydrocyclones. Centrifugation can be carried out in any known centrifuge which works batchwise or continuously. It is very advantageous to use push air centrifuges which can be operated in one or more stages. Also suitable are screw sieve centrifuges or screw discharge centrifuges (decanters). A filtration is advantageously effected by means of press filters which can be operated batchwise or continuously, with or without stirrer or by means of belt filters. In general, filtration can be effected under superatmospheric pressure or under reduced pressure.

The solid-liquid separation may be accompanied and/or followed by further process steps for increasing the purity of the crystals or of the crystal cake. In a particularly advantageous embodiment of the invention, the separation of the crystals from the mother liquor is followed by a single- or multiple-stage washing and/or sweating of the crystals or of the crystal cake. In washing, the quantity of wash liquor is suitably within the range from 0 to 500 g of wash liquor/100 g of crystallizate, preferably within the range from 30 to 200 g of wash liquor/100 g of crystallizate. The wash liquor used is not subject to any restriction. It is advantageous, however, to wash with pure product, ie. with an acrylic or methacrylic acid liquid whose purity is greater than that of the crystal cake to be washed. A wash with water is also possible. The wash can take place in customary apparatus for the purpose. It is advantageous to use wash columns in which the removal of the mother liquor and the washing take place in one and the same apparatus, centrifuges, which can be operated in one or more stages, or press filters or belt filters. The washing can be carried out on centrifuges or belt filters in one or more stages. The wash liquor can be passed in countercurrent to the crystal cake.

Sweating describes a local melting-off of impure regions. The sweat quantity is advantageously within the range from 0 to 100 g of molten-off crystallizate/100 g of crystallizate prior to sweating, preferably within the range from 5 to 35 g of molten-off crystazizate/100 g of crystallizate. It is particularly preferable to carry out the sweating on centrifuges or belt filters. A combined wash and sweat in one apparatus can also be suitable.

The acrylic acid crystals and methacrylic acid crystals after the solid-liquid separation and any further washing and/or sweating constitute the purified acid obtained from the process. The purity of the crystals obtained is generally within the range from 97 to 99.99% by weight of acrylic acid or methacrylic acid, especially within the range from 98.5 to 99.9% by weight of acrylic acid or methacrylic acid. The crystals prepared by the process of the present invention include only very minimal amounts of impurities, such as acetic acid, maleic acid or aldehydes.

If desired, the purified acid can be esterified by known methods or further purified by known methods. In an advantageous embodiment of the invention, step (d) is followed by step (e) explained below.

Step (e)

Step (e) recycles the mother liquor which remains after the crystals have been separated off, at least partly directly into the crystallization step (c). The proportion of recycled mother liquor is within the range from 0 to 100% by weight, preferably within the range from 20 to 80% by weight.

The figure illustrates a preferred embodiment of the process of the present invention. The line 2 and compressor 3 supply air to the synthesis reactors 4 and 5. In addition, reactor 4 is supplied via line 9 with recycled gas which has been compressed by compressor 6 and which consists essentially of nitrogen, carbon oxides and unconverted starting materials, together with propene or isobutene from line 1. The synthesis reactor 4 is where the first stage of the two-stage gas phase oxidation, namely the oxidation of propene or isobutene to the corresponding acrolein, takes place. The acrolein is then oxidized to the corresponding acid in synthesis reactor 5. This gives rise to a gaseous product mixture which, as well as the acid, comprises impurities mentioned above. This gaseous product mixture is fed via line 7 to the condenser 8, where it is cooled down and condensed to a solution. The uncondensed portion of the product mixture is removed via line 9, with a portion being recycled as recycled gas, as described above, into reactor 4, while the other portion, preferably 50% of the total stream of line 9, is removed from the plant as a waste gas via line 10. The solution formed in the condenser 8 is fed via line 11 to the crystallizer 12, where the crystallization is carried out. The mother liquor of the crystallization is fed together with the crystallizate via line 13 to a suitable apparatus 14 for solid-liquid separation, the crystallizate being removed via line and the mother liquor via line 16. In a preferred embodiment, at least some of the mother liquor is reintroduced via line 17 into the crystallization step (in line 11 and crystallizer 12). Thus, the purified crude acid is removed via line 15.

The process of the present invention has the advantage over existing processes that, after condensation of the product mixture produced in the gas phase oxidation, the solution formed in the condensation yields a very high quality crude acid directly by crystallization. When using a crystallization having more than one purification stage, it is possible to produce a pure acid directly, without a prepurification having to be carried out in departure from the above-cited references, Canadian Patent 790 625, JP-A-7 082 210 and EP-A-0 616 998.

It is a further important advantage of the process of the present invention that the process is carried out at a relatively low temperature, ie. that the main stream of acrylic acid or methacrylic acid is removed directly as product via condensation and crystallization. Since, in contradistinction to the prior art, no assistant is added and thus no high thermal stress (especially in the case of high acid contents) is needed to remove this assistant, polymerization problems and the use of process stabilizers as in the prior art are minimized. In addition, fouling is avoided or reduced as well as a result. It is surprising that it is possible to crystallize acrylic acid solutions or methacrylic acid solutions obtained by gas phase oxidation and condensation directly and that the products obtained have very high purity. It is particularly surprising that this is possible with aqueous condensates.

The Example which follows, which describes a preferred embodiment of the invention, illustrates the invention.

EXAMPLE

A 31 stirred vessel made of glass (jacket, helical stirrer) was charged with 2.3 kg of the following mixture: 77.8% by weight of acrylic acid, 4.01% by weight of acetic acid, 1.07% by weight of maleic acid, 3.66% by weight of formaldehyde and 13.46% by weight of water. This mixture corresponds in the drawing of the figure to the stream in line 11 which comes from condenser 8. This solution was cooled from room temperature down to −0.9° C. by cooling via the jacket of the crystallizer. The first acrylic acid crystals formed at this temperature. The further cooling down to −4.4° C. took 3 h 54 min. A solids content of 35.5 g of solids/100 g of suspension was obtained at that temperature. 218.7 g of the suspension were separated at −4.4° C. on a centrifuge at 2000 rpm in the course of a whirling time of 1 min into 77.76 g of crystals and 140.94 g of mother liquor. The crystals were then washed for 1 min on the centrifuge with 40 g of pure acrylic acid having an acrylic acid content of more than 99.6%.

Analysis of the crystals revealed the following composition:

| | |
|---|---|
| Acrylic acid | 98.97% by weight |
| Acetic acid | 0.321% by weight |
| Maleic acid | 0.0204% by weight |
| Formaldehyde | 0.1190% by weight |
| Water | 0.43% by weight |

The process of the invention thus provides an acrylic acid which is high in purity compared with the feed acrylic acid.

We claim:

1. A process for preparing acrylic acid or methacrylic acid, comprising:
   (a) providing a gaseous reaction product mixture having essentially the composition of a reaction mixture of the catalytic gas phase oxidation of at least one member selected from the group consisting of $C_3$-/$C_4$-alkanes, alkenes, alkanols, alkanals, and precursors thereof, to form acrylic acid or methacrylic acid,
   (b) condensing said gaseous reaction product mixture to form a solution, (c) crystallizing acrylic acid or methacrylic acid from a solution consisting essentially of the solution obtained in step (b), to form crystals of acrylic acid or methacrylic acid and a mother liquor, and (d) removing the crystals from the mother liquor.

2. A process as claimed in claim 1, wherein said gaseous product mixture of step (a) is prepared by catalytic gas phase oxidation of propene, acrolein, tert-butanol, isobutene, isobutane, isobutyraldehyde, methacrolein, isobutyric acid or methyl tert-butyl ether.

3. A process as claimed in claim 1, wherein step (b) is effected in one or more stages as a partial or total condensation.

4. A process as claimed in claim 1, wherein step (c) is effected in one or more stages.

5. A process as claimed in claim 1, wherein step (c) is effected at a temperature of said solution within the range from −25° C. to +14° C.

6. A process as claimed in claim 1, wherein step (c) is effected by removing the heat by cooling apparatus walls or by evaporating said solution under reduced pressure.

7. A process as claimed in claim 1, wherein said crystals are removed from said mother liquor by at least one step selected from the group consisting of filtration and centrifugation.

8. A process as claimed in claim 1, wherein said crystals removed in step (d) are further subjected to at least one step selected from the group consisting of a washing step and a sweating step.

9. A process for preparing acrylic acid or methacrylic acid, comprising:

(a) providing a gaseous reaction product mixture having essentially the composition of a reaction mixture of the catalytic gas phase oxidation of at least one member selected from the group consisting of $C_3$-/$C_4$-alkanes, alkenes, alkanols, alkanals, and precursors thereof, to form acrylic acid or methacrylic acid, (b) condensing said gaseous reaction product mixture to form a solution, (c) crystallizing acrylic acid or methacrylic acid from a solution consisting essentially of the solution obtained in step (b) and the portion of the recycled mother liquor of step (e), to form crystals of acrylic acid or methacrylic acid and a mother liquor, (d) removing the crystals from the mother liquor, and (e) recycling at least a portion of said mother liquor from step (d) into step (c).

10. A process as claimed in claim 9, wherein said gaseous product mixture is prepared by catalytic gas phase oxidation of propene, acrolein, tert-butanol, isobutene, isobutane, isobutyraldehyde, methacrolein, isobutyric acid or methyl tert-butyl ether.

11. A process as claimed in claim 9, wherein step (b) is effected in one or more stages as a partial or total condensation.

12. A process as claimed in claim 9, wherein step (c) is effected in one or more stages.

13. A process as claimed in claim 9, wherein step (c) is effected at a temperature of said solution within the range from −25° C. to +14° C.

14. A process as claimed in claim 9, wherein step (c) is effected by removing the heat by cooling apparatus walls or by evaporating said solution under reduced pressure.

15. A process as claimed in claim 9, wherein said crystals of step (d) are removed from said mother liquor by at least one step selected from the group consisting of filtration and centrifugation.

16. A process as claimed in claim 9, wherein said crystals removed in step (d) are further subjected to at least one step selected from the group consisting of a washing step and a sweating step.

17. A process as claimed in claim 9, wherein step (e) is effected by recycling from 20 to 80% by weight of said mother liquor into step (c).

18. The process of claim 1, wherein said solution in (b) comprises at least 93% by weight acrylic acid or methacrylic acid.

19. The process of claim 1, further comprising addition of a process stabilizer.

20. The process of claim 9, wherein said solution in (b) comprises at least 93% acrylic acid.

21. The process of claim 9, further comprising addition of a process stabilizer.

* * * * *